United States Patent [19]

Ersek et al.

[11] Patent Number: 5,336,263
[45] Date of Patent: Aug. 9, 1994

[54] TREATMENT OF UROLOGICAL AND GASTRIC FLUID REFLUX DISORDERS BY INJECTION OF MMICRO PARTICLES

[75] Inventors: Robert A. Ersek, 62 Pascal, Austin, Tex. 78746; Arthur A. Beisang, 1300 Ingerson Rd., Arden Hills, Minn. 55112; Arthur A. Beisang, III, 5883 Carlson St., Shoreview, Minn. 55126

[73] Assignees: Robert A. Ersek, Austin, Tex.; Arthur A. Beisang, Shoreview; Arthur A. Beisang, III, St. Paul, both of Minn.

[21] Appl. No.: 52,234

[22] Filed: Apr. 22, 1993

Related U.S. Application Data

[63] Continuation of Ser. No. 863,848, Apr. 6, 1992, abandoned.

[51] Int. Cl.$^5$ ............................................. A61F 2/02
[52] U.S. Cl. .................................... 623/11; 623/66; 600/29
[58] Field of Search ................... 623/11, 12, 16, 66, 623/8; 600/29, 30

[56] References Cited

U.S. PATENT DOCUMENTS

| | | |
|---|---|---|
| 3,638,649 | 5/1972 | Ersek . |
| 3,657,744 | 4/1972 | Ersek . |
| 4,061,731 | 11/1977 | Gottlieb . |
| 4,093,576 | 6/1978 | deWijn ............................ 260/17 R |
| 4,138,382 | 2/1919 | Polmanteer . |
| 4,186,189 | 1/1980 | Shalaby et al. ........................ 424/78 |
| 4,197,846 | 4/1980 | Bucalo ................................. 128/488 |
| 4,212,857 | 8/1980 | Balassa et al. . |
| 4,239,492 | 1/1981 | Holman et al. . |
| 4,240,794 | 1/1981 | Holman et al. . |
| 4,341,691 | 8/1982 | Anuta . |
| 4,424,208 | 1/1984 | Wallace et al. . |
| 4,469,676 | 9/1984 | Hecmati ............................... 424/95 |
| 4,565,580 | 1/1986 | Miyata et al. . |
| 4,582,640 | 4/1986 | Smestad et al. . |
| 4,592,864 | 6/1986 | Miyata et al. . |
| 4,631,188 | 12/1987 | Stoy et al. . |
| 4,652,441 | 5/1987 | Okada et al. . |
| 4,773,393 | 9/1988 | Haber et al. . |
| 4,803,075 | 2/1989 | Wallace et al. ...................... 424/423 |
| 4,828,827 | 5/1989 | Henderson et al. .................. 424/80 |
| 4,837,285 | 6/1989 | Berg et al. ........................... 530/356 |
| 4,882,607 | 11/1989 | Balassa . |
| 4,894,231 | 1/1990 | Moreau et al. . |
| 5,011,494 | 4/1991 | von Recum et al. . |
| 5,067,965 | 11/1991 | Ersek et al. . |
| 5,077,940 | 4/1991 | Berg ..................................... 423/66 |

FOREIGN PATENT DOCUMENTS

| | | |
|---|---|---|
| 0022724 | 1/1981 | European Pat. Off. . |
| 0206726 | 12/1986 | European Pat. Off. . |
| 0251695 | 1/1988 | European Pat. Off. . |
| 3038047 | 10/1980 | Fed. Rep. of Germany . |
| 86/03671 | 12/1985 | PCT Int'l Appl. . |
| 87/05521 | 9/1987 | PCT Int'l Appl. . |
| 88/06873 | 9/1988 | PCT Int'l Appl. . |
| 88/07355 | 10/1988 | PCT Int'l Appl. . |
| 2139898 | 11/1984 | United Kingdom . |
| 2227176 | 7/1990 | United Kingdom . |

OTHER PUBLICATIONS

Ersek, R. A., et al "Bioplastique: A New Textured Copolymer Micro Particle Promises Permanence in Soft Tissue Augmentation", Plastic & Reconstructive Surgery, vol. 87, No. 4, pp. 693-702, Apr. 1991.

Harwicke, J., Advances in Nephrology, 2:61-74, 1972.

Malizia et al., JAMA, vol. 251, No. 24, pp. 3277-3281 (1984).

Rhodes, J. E., "Various plasma expanders in man", Annual, New York Academy of Science, 55:522-525, 1952.

(List continued on next page.)

Primary Examiner—David Isabella
Attorney, Agent, or Firm—Haugen and Nikolai

[57] ABSTRACT

Novel principles for treating urological and gastric fluid reflux disorders are disclosed wherein textured micro particles having a combination of average unidimensional particle size range and average particle texture which cooperate substantially to prevent loss of the micro particles from any injection site.

20 Claims, 3 Drawing Sheets

OTHER PUBLICATIONS

O'Donnell and Puri, "Technical refinements in endoscopic correction of vesicoureteral reflux", *The Journal of Urology*, vol. 140, Nov., 1988, pp. 1101–1102.

Balazs, E A., et al, "The Replacement of the Vitreous Body in the Monkey by Reconstituted Vitreous and by Hyaluronia Acid", Surgery of Retinal Vascular Diseases, Colloque, Amerstoort 1963, *Mod. Probl. Ophthal.*, 4:230–232 (Karger, Basel/New York 1966).

Mentor O&O Inc. "Mentor Polytef Paste" package labeling.

Bradley and Timm, "Treatment of urinary incontinuence by implantable prosthetic sphincter", *Urology*, 1:252 (1973).

Landes, E., "Application Modalities and Experiences with Collagen in the Treatment of Folds and Scars", Z. Hautkr. 60, Heft 16 (1985).

Schnitzler, L. R. Baran, M. Arrouy, L. Dubertret, and M. Haslan, "Responses Cutanees a L'Implant de Collegene Injectable (Zyderm)", *Ann. Dermatol. Venereol.*, 111, No. 2 (1984).

Arnold, Godfrey E., "Vocal Rehabilitation of Paralytic Dysphonia", *Archives of Otolaryngology*, 62:1–17 (1965).

Kaufman, "Treatment of post-prostatectomy urinary incontinence using a silicone gel prosthesis", *Brit. J. Urol.*, 38:646 (1973).

Kaufman, "Treatment of post-prostatectomy urinary incontinance using a gel prosthesis", *Brit. J. Urol.*, 45:646 (1973).

Kojima, M. Takahashi, K. and Honda, K., "Morphological study on the effect of polyvinyl pyrrolidone infusion upon the retino-endothelial system", *Tokyo J. Exp. Med.*, 92:27–54 (1967).

Matouschek, E., "Treatment of Vesicorenal Reflux by Transurethral Teflon-Injection", Urologe A, 20:263–264 (1981).

*Fig. - 8*

TREATMENT OF UROLOGICAL AND GASTRIC FLUID REFLUX DISORDERS BY INJECTION OF MMICRO PARTICLES

CROSS-REFERENCE TO RELATED APPLICATION

This is a continuation of copending application Ser. No. 07/863,848, filed on Apr. 6, 1992 now abandoned.

Cross reference is made to a related application of common inventorship and assignee, Ser. No. 07/714,273, filed Jun. 12, 1991, now U.S. Pat. No. 5,258,028 which in turn is a continuation-in-part of Ser. No. 07/282,671, filed Dec. 12, 1988, now abandoned.

BACKGROUND OF THE INVENTION

I. Field of the Invention

This invention is directed generally to the permanent augmentation of soft tissue and, more particularly, to the treatment of urological disorders, e.g., incontinence, vesicoureteral reflux, gastric fluid reflux, etc., by endoscopic injection of compatible micro particle implants into the submucosal tissue. Since the invention is closely related to the treatment of incontinence, it will be described in detail by reference thereto.

With the exception of urinary incontinence secondary to neurogenic disorders, incontinence occurs when the resistance to urine flow has decreased excessively, i.e., urethral resistance to urine outflow, from whatever cause, has been lowered to the point when it can no longer resist increased intra-abdominal pressure. While this may seem to be an oversimplification of the problem, in general nearly all procedures developed to restore continence are designed on this basis to restore the lost resistance to urine outflow. Similarly, the present invention allows for the control of gastric fluid reflux when submucosal injections of the micro implants are made to the esophageal-gastric junction and to the gastric-pyloric junction.

To these ends, several surgical procedures and devices have heretofore been developed and tried with varying degrees of success, e.g., suspension procedures, plications, constrictive procedures and various combinations of these. Devices which have been developed primarily operate as plugs and cannot be used on a permanent basis. Electrical stimulation and biofeedback techniques have so far been demonstrated to have limited success in treatment of incontinence and gastric reflux.

II. Discussion of the Related Art

As examples of such treatments and procedures heretofore known in the art, mention may be made of a variety of prosthetic devices based on the compression of the urethra at a given point. (See, for example, "Treatment of urinary incontinence by implantable prosthetic sphincter," by Bradley and Timm, *Urology*, 1:252 (1973); "Treatment of post-prostatectomy urinary incontinence using a gel prostheses", by Kaufman, *Brit. J. Urol.*, 45:646 (1973) and "Treatment of post-prostatectomy urinary incontinence using a silicon gel prostheses", *Brit. J. Urol.*, 48:646 (1973).

In the practice of plastic and reconstructive surgery, inert materials have frequently been implanted to fill in defects or augment weakened tissue. These have been fabricated of a variety of materials and have been implanted using several techniques.

Certain very small particle species compounded in a lubricious material have been implanted by subcutaneous injection for both soft and hard tissue augmentation. Heretofore success has been limited. Undesirable subsequent particle migration and serious granulomatous reactions have commonly resulted. This is well documented with such materials as polytetrafluoroethylene (PTFE) particles of very small diameter (>90% of a diameter <30 microns) in glycerine. One such product includes PTFE particles, suspended in glycerine with a minor amount of polysorbate is available under the name Polytef® (trademark of Mentor Corp. of California). This is discussed, for example, in Malizia, et al., *JAMA*, Volume 251, No. 24, pp. 3277–3281 (1984).

U.S. Pat. No. 4,773,393 issued Sep. 27, 1988 to Haber and Malizia and assigned to C.R. Bard, Inc. relates to an apparatus for hypodermically implanting a genitourinary prosthesis comprising an extensible, inflatable tissue expanding containment membrane to be located in the proximal periurethral tissues to add bulk to these tissues and thereby overcome urinary incontinence by means of localized, controlled tissue volume increase. In column 1, reference is made to the aforementioned *JAMA* article co-authored by the co-patentee Anthony A. Malizia with respect to the widespread migration of polytef particles along with granulomas. Accordingly, the patented invention is said to obviate these problems by providing a prosthesis comprising an elastomerical biocompatible containment membrane into which a biomeric fluid or suspended particulate matter such as TEFLON particles is percutaneously injected to inflate the membrane.

The use of very small diameter particulate spheres (approximately 1–20 microns) or small diameter elongated fibrils, (generally 1–20 microns in diameter) of various materials such as cross-linked collagen or synthetic polymers suspended in an aqueous medium to which a biocompatible fluid lubricant has been added as injectable implant composition is disclosed in Wallace et al., U.S. Pat. No. 4,803,075. While these materials create immediate augmentation, this result is generally short-lived as the material also has a tendency to migrate and/or be reabsorbed from the injection site by the host tissue.

Most recently, three companies have indicated in published reports their intent to enter the market for treatment of urinary incontinence with an injectable material. Mentor Corporation has received limited approval from the FDA for use of their injectable material, "Urethrin", in treating incontinent male postprostatectomy patients. Previous published reports stated that C.R. Bard, Inc. and Collagen Corporation were developing an incontinence treatment called "Contigen Bard Collagen Inplant," understood to be Collagen Corporation's "contigen" injectable bovine collagen material. Subsequently, it was reported that C.R. Bard is also evaluating for urinary incontinence treatment a product called "Hylagel-Muscle" which is said to be based upon Biomatrix's patented technology on modifying naturally occurring hyaluronan "to form three-dimensional sponge-like matrixes in the form of high molecular mass fluids, gels and solids that can separate tissue, cells and molecules."

From the foregoing survey of the current state of the art, it will thus been seen that of recent date many approaches and treatments have been proposed to cure or relieve conditions of urinary incontinence by injection. While some of these approaches have enjoyed modest success, relief has been, for the most part, only temporary in those patients where success is noted. This generally is due to granuloma reactions and/or migration of injected particulate material and reabsorption of gellular materials. Thus, there remains a very important need for a treatment that will provide a lasting remedy for successfully treating such urological disorders.

SUMMARY OF THE INVENTION

The present invention provides an improved method for treating urological disorders such as stress incontinence and gastric fluid reflux disorders, by injecting endoscopically a biocompatible fluid vehicle containing non-absorbable polymeric, particulate micro-implants which are characterized as being biocompatible, immunologically non-reactive and which will take advantage of the body's own mechanism to encapsulate the micro-implanted particles to prevent migration from the injection site. In accordance with the present invention, the aforementioned tasks are solved in an elegant manner by the endoscopic injection of regularly or irregularly shaped, textured or relatively smooth micro particles combined with a biocompatible fluid vehicle.

The textured micro particles have a nominal unidimensional measurement of between about 30 and 3000 microns (0.003 to 3.0 mm), and a preferred range for most applications is between about 80 and 600 microns (0.008 to 0.6 mm). The textured micro particles present generally amorphous surfaces, and normally possess surface irregularities including indentations ranging in size from, for example, 10Å (angstroms) to 500 microns, with the indentations themselves having irregular configurations and surfaces. A minimal inter-indentation distance is maintained that enables the particles to be injected through an hypodermic needle of the appropriate preselected size, and with or without a physiologic vehicle.

Examples of appropriate physiologic vehicles are saline, solutions of sodium hyaluronate, various starches, hydrogels, polyvinylpyrrolidones, other polymeric materials, polysaccharides, organic oils or fluids, all of which are well known and utilized in the art. Vehicles that are biologically compatible, i.e., cause minimal tissue reaction and are removed or metabolized without cytotoxicity, are, of course, preferred. Biologically compatible saccharides such as glucose have been found useful, aqueous solutions of starch or sodium hyaluronate may be employed and certain fats may also be found useful. In certain instances, it may be desirable to employ a totally inert vehicle. The patient's own plasma may be derived from blood withdrawn from the patient, centrifuged to remove cells (or not) and mixed with appropriate aliquots of particles and the mixture injected in the desired locations.

In this connection, highly compatible vehicles include esters of hyaluronic acids such as ethyl hyaluronate and polyvinylpyrrolidone (PVP). PVP normally has the general empirical formula $[(CHCH_2)_2N(CH_2)_3CO]_n$ wherein n equals 25–500, a form of which is otherwise known and marketed as Plasdone ™ (trademark of GAF Corporation, New York, N.Y.). Additionally, polyvinylpyrrolidone (Plasdones), hyaluronate, collagen and other biocompatible substances may be incorporated into the elastomer or combined with its surface.

In certain instances, it has been found desirable to utilize a surface modifier in combination with the micro particles, with materials such as polyvinylpyrrolidone, polytetrafluoroethylene, collagen, or hyaluronates having been found suitable. In this connection, the surface modifiers may be mixed into the substance of or with the micro particles, and furthermore may thereafter be coated with a layer of a hyaluronate or hyaluronic acid. Specifically, certain modifiers such as polytetrafluoroethylene may be admixed with, for example, a poly di-substituted siloxane particle material prior to cure to impart an average surface modification to the cured particle. A material such as hyaluronic acid may be attached to the micro particle surface either through physical or chemical bonding. Surface modifiers also can be used to typically assist in detoxification and promote the desired tissue ingrowth encapsulation. Other bioactive substances that can be included in the carrier or attached to the surface of the beads to promote encapsulation include fibronectin, n, transforming growth factor beta, and various other cytokines such as interleukin-1.

DETAILED DESCRIPTION

As heretofore mentioned, the present invention is directed to the treatment of urological and gastric fluid reflux disorders, particularly stress incontinence, by endoscopic injection of specified micro particles. The above-referenced copending application relates to an improved micro-implantation method and composition for filling depressed scars, unsymmetrical orbital floors, muscle, lip, and other tissue defects in reconstructive surgery procedures. The tissues to be augmented exhibit varying degrees of softness.

As disclosed, textured micro particles having an outside diameter between about 30 microns and 3000 microns are employed with an appropriate physiologic vehicle, as will be detailed hereinafter. A more preferred range is above about 80 microns and depending on the precise application between about 80 to 100 and 600 microns. Equivalent smooth particles should be somewhat larger.

In accordance with the invention, the particles are preferably injected through a hypodermic needle of an appropriate preselected size, preferably with an appropriate lubricious physiologic vehicle which is biocompatible, i.e. causes minimal tissue reaction and is removed or metabolized without cytotoxicity. As indicated above, and by way of illustration, possible suitable useful disclosed physiologic vehicles include, saline, various starches, hydrogels, polyvinylpyrrolidones (Plasdones), polysaccharides, fats, organic oils or fluids and other polymeric materials, all of which are well known and utilized in the art. In this connection, highly compatible vehicles also include esters of hyaluronic acids such as ethyl hyaluronate and polyvinylpyrrolidone (PVP). PVP normally has the general empirical formula $[(CHCH_2)_2N(CH_2)_3CO]_n$ wherein n is in the range of about 25–500, a form of which is otherwise known and marketed as Plasdone TM, or the patient's own plasma.

Additionally, polyvinylpyrrolidone (Plasdones), hyaluronate, collagen and other biocompatible substances may be incorporated into the elastomer or combined with its surface. As used herein, a "surface modifier" connotes a material combined into the formed particle, applied to the surface of the particle or added to the carrier vehicle to alter inter-particle or prosthesis-host interaction and/or particle identifiability. These surface modifiers may alter the coefficient of friction of the particles, as by making them more lubricious, render the particles more radiopaque, assist in detoxification, and/or render the surface of the particles more susceptible to tissue ingrowth or facilitate tissue encapsulation of individual particles. Useful surface modifiers include PVP, collagen, hyaluronates, polytetrafluoroethylene, and others.

The surface modifiers such as polyvinylpyrrolidone or polytetrafluoroethylene may be mixed into the substance of or with the micro particles, which furthermore may thereafter be coated with a layer of a hyaluronate or hyaluronic acid. Specifically, certain modifiers such as polytetrafluoroethylene may be admixed with, for example, a poly di-substituted siloxane particle material prior to cure to impart an average surface modification to the cured particle. A material such as hyaluronic acid may be attached to the micro particle surface either thorough physical or chemical bonding. Surface modifiers also typically are selected to assist in detoxification and promote the desired tissue encapsulation. As mentioned above, other bioactive substances that can be included in the carrier or attached to the surface of the micro implants to promote encapsulation include fibronectin, n, transforming growth factor beta, and various other cytokines such as interleukin-1.

Once implanted, the body will form a thin scar tissue around each of the implants so as to provide initial encapsulation. Polyvinylpyrrolidone, hyaluronate or collagen or other biocompatible substances may be chemically or physically combined with the particle substance or its surface to enhance the acceptance of the implant by the host. While in most situations the particles are of random size and configuration, but within the constraints of size indicated, it is generally desirable that the particles be of generally uniform configuration for use in a given procedure. With respect to relative resilience of the augmentation mass, it is preferably designed to closely simulate the tissue of the implant or injection site.

For soft tissue, a soft elastomer such as silicone rubber is a desirable material for the textured particles. This is preferably a poly(dimethylsiloxane) but may have substitute alkyl or aromatic groups. When a firm area is being treated, such as connective tissue or the like, polytetrafluoroethylene (Teflon) or polyethylene may be satisfactorily utilized. In those instances wherein the requirement is for hard substances, biocompatible materials such as certain calcium salts including hydroxyapatite or other such crystalline materials, biocompatible ceramics, biocompatible metals such as certain stainless steel particles, or glass may be utilized.

By way of further background, the average diameter of a capillary is approximately 16 microns, or roughly two times the diameter of a red cell. Therefore, since the size of the textured micro particles is in the area of at least approximately 30 microns, they will not be absorbed into the capillaries, but will on the other hand, remain generally captive and fixed in place. Smaller particles, including some in the sub-micron range, have been implicated in causing chronic inflammation and may be ingested by host cells. Thus, particles in the range of between about 30 and 3000 microns are employed.

The fibroblast cell is the scar-forming cell of the human body, and these cells range in size from between about 20 microns up to about 100 microns, and because of contact guidance and reduced micromotion, they will form an efficient scar tissue or collagen-based coating around an inert foreign body. Furthermore, such scar tissue will conform to the irregularities in the surface of the foreign body, particularly if they are of sufficient size to accommodate tissue ingrowth. Our previous studies (American Society of Artificial Internal Organs; U.S. Pat. Nos. 3,638,649; 3,657,744; 4,239,492; and 4,240,794) have shown that foreign substances can be substantially firmly anchored in a predetermined location in the body. Because of the inherent ability of fibroblasts to form scar tissue in and around irregularities of the surface, such anchoring occurs in many locations, including locations within the blood stream.

Figure 1:
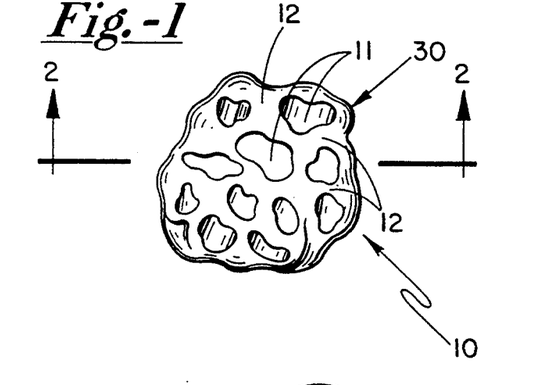
FIG. 1 is a perspective view of a micro particle useful in accordance with the present invention, and illustrating surface irregularities typically present in the particle.

FIG. 1 illustrates a micro-implant particle generally designated 10 which has an inner-core having various randomly distributed indentations or pores 11—11 throughout its surface. These openings or pores are spaced apart by connective pillar members 12. As indicated above, the indentations, interstices or pores preferably have a minimum indentation depth or open dimension of about 10 Angstroms, along with a maximum dimension of about 500 microns. The interconnective or pillar zones 12—12 which separate or otherwise define solid material between openings or indentations 11—11 have a dimension or breadth sufficient so that the majority or greater portion of the surface is defined by indentations, openings or pores.

Figure 8:
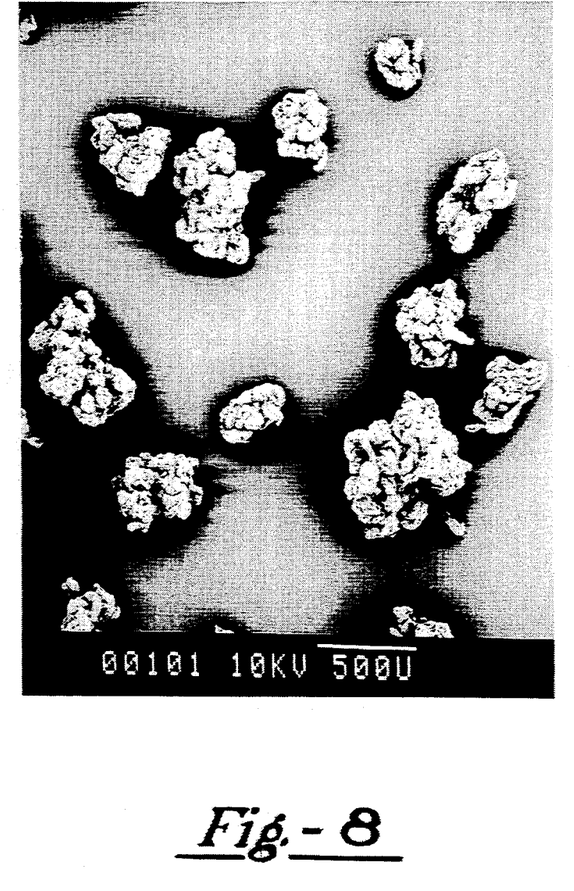
FIG. 8 is an actual photomicrograph of particles useful in accordance with the invention.

Actual particles are shown in the photomicrograph of FIG. 8. As can be seen from the scale of the Figure, the size range of the illustrated particles ranges from about 100 to 600 microns. The irregular particle shapes and surface configurations including indentations, openings and pores is dramatically illustrated.

Figures 2, 3:
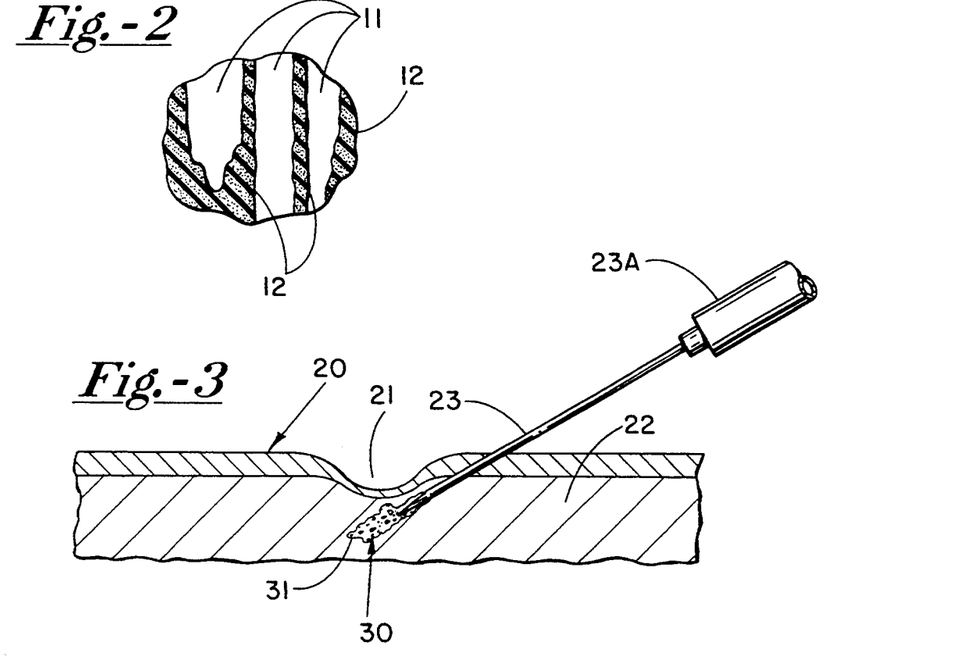
FIG. 2 is a vertical sectional view taken along the line and in the direction of the arrows 2—2 of FIG. 1.
FIG. 3 is a schematic illustration of a fragmentary portion of human skin organ, and illustrating a hypodermic needle of appropriate size being utilized to introduce materials in accordance with the present invention into the subcutaneous zone beneath a depressed scar.

With continued attention being directed to FIGS. 1 and 2 of the drawings, connective elements 12 are available on the surface of the micro-implant particles and provide for mechanical stability of the individual particle. This arrangement is illustrated in particular in FIG. 2 and is apparent from the photomicrograph of FIG. 8.

As further disclosed in the cross-referenced application, it has been found that inert foreign tissue augmentation particulate matter having a mean diameter less than about 30 microns will generally become subject to significant migratory loss from the site of injection, regardless of surface configuration absent extraordinary protection. The textured or irregular nature of the surface of the microspheres of the invention, however, imparts to them an apparent size equivalency which, in the case of at least the relatively smaller sized particles (particularly in the range of 30–60 and up to 80 microns), makes them behave, once injected, as much larger smoother particles might behave with respect to host implant or prosthesis migration tendencies and benign assimilation in scar tissue. Particulate matter of the class of the present invention which is of a size ranging from about 30 microns to about 3000 microns and having a textured surface in which the surface irregularities vary in size over a range of about 10 Angstroms to 500 microns.

The irregularities, pores and interstices are designed to have widths ranging from those having a diameter or opening size which will just accommodate the infiltration of a typical connective tissue fibril or protein molecule at the lower end to those large enough to accommodate ingrowth of much larger cross-linked protein, possibly collagen protein, fibrillar structures or actual fibroblasts at the high end. In this regard, it is well known that the collagen fiber is composed of fibrils and filaments. The basic poly-peptide chain is arranged into micro-filaments of tropocollagen having a diameter of approximately 20 Angstroms. It has been found that surface irregularities as small as 10 Angstroms will interdigitate with the filaments on the surface of the fibers and serve to resist host-prosthesis interface motion.

Further, with respect to particle size, it will be appreciated that particle size, particularly of those species contained in preparations utilized in prior injectable compositions, tends to vary over a range within any group of particles so that there will be a percentage of the group larger and a percentage of the group smaller than at target size of the indentations, pores or interstices associated with a give group of particles will also describe a range. It will further be appreciated that one must take into account the normal variation in patient-to-patient acceptance and reaction to tissue augmentation injection of micro particles. With this in mind, certain observations have been made regarding optimum particle size, particularly with regard to the severe problems of unwanted migration and formation of granulomatous reactions.

Observations in a variety of clinical situations indicate that particles less than about 60 microns in diameter can be engulfed by macrophages and transported to regional lymph nodes. Submicron-sized particles may be the most easily transported and may remain intracellular indefinitely. However, larger particles, particles that approach the size of a macrophage, i.e., from about 20 to about 60 microns, may cause the death of a cell when engulfed. This begins a progression in which the dead cell releases its intercellular enzymes (cytokines), and those attract other phagocytes which, again, encounter and engulf the particle with the debris of the first encounter. In this manner, a vicious cycle continues on a larger scale as a chronic inflammatory response. Of course, such a response is highly undesirable.

Particles greater than about 60 microns, however, have not been observed within a cell or within lymph nodes; and, certainly, particles greater than 80 microns appear safe from initiating such foreign body reactions. Further, as in the example below, particles of an average diameter of 100 to 600 microns with textured surfaces having an average indentation cavity or pore size from about 10 microns to about 200 microns have been observed to work quite well. Theoretically, there is no upper limit to the size of the textured particles, and this is borne out by the success of sintered-surface hip implants, textured breast implants and others. However, the useful upper limit of micro implant dimensions is probably somewhere in the vicinity of 1 to 3 mm in defects just beneath the skin surface because particles of a size greater than this may be perceived as surface irregularities when palpitated. Large textured implants have also been employed in breast reconstruction, for example.

It will be appreciated that textured spheroids of the class contemplated for use in the present invention may be molded, for example, by any gravity-free technique wherein the spheroids are formed with centrifugal force equal to that of gravity in cases where the spheroids are formed of rather malleable synthetic material. Spheroids can be fabricated from a variety of inert substances such as polytetrafluoroethylene, poly(methylmethacrylate), poly substituted siloxanes (silicones) and a variety of other synthetic polymeric materials, ceramics and others and different fabrication processes may be applicable to each material for the augmentation of soft tissue. Of course, fabrication of the spheroids from a malleable polymer material such as a silicone rubber is preferred as it will more closely imitate the texture of the natural tissue it replaces. With respect to malleable polymers such as silicone rubber, the following fabrication techniques are exemplary of those that will readily enable manufacture by those skilled in the art. It will be appreciated that a technique that might be preferred for one material may not work equally well for all.

In one process, a malleable stock of unvulcanized polydimethylsiloxane is rolled into spheroids of approximately 100 microns or other desired size diameter. The surface is then textured by impacting each spheroid with an appropriate force. The textured spheroids are then vulcanized and mixed with the appropriate vehicle for injection.

In another successful method, generally preferred for forming beads of silicone rubbers, poly(di-substituted siloxane) may be dispersed in an appropriate volatile solvent and then partially cured by droplets being forced through a specific distance of air from an orifice having a specific diameter. This is a very familiar process technique generally known with respect to the operation of a shot tower in making lead shot. The size of the particles or spheroids is easily regulated by varying the viscosity of the mixture and/or the orifice of origin. As the particle travels a known distance through air, it is partially cured as the volatile vehicle evaporates. The specifically formed spheroid or bead is then separated by a suitable fluid medium. The spheroids may then be pressed against an appropriate surface or impacted by an appropriate force to impart the desired texture, the surface having an appropriate mold release. Partially cured spheroids are then vulcanized by heat irradiation. The particles are then sized and graded by physical means. Spheroids are then mixed with the appropriate vehicle in appropriate ratios, placed in containers and finally sterilized within the container.

Texture can be imparted to the beads or spheroids in a number of ways. In addition to the molding method, other techniques include ion-beam microtexturing which makes it possible to produce controlled microtextured surfaces, chemical and plasma etching and impacting the beads with solid particles. Of course, it is contemplated that other methods could also occur to those skilled in the art.

If desired, surface modifiers, as explained above, can be incorporated in the material prior to formation of the spheroids or beads or may be thereafter be added as a coating on the deformed surfaces. In this manner, certain materials such as hyaluronic acid, for example, may be attached to the micro particle surface either through physical or chemical bonding in a well-known manner after formation and texturing.

EXAMPLE I

Amounts of particles with average diameters of 100, 150 and 600 micrometers were fabricated with a textured surface from fully polymerized and vulcanized poly(dimethylsiloxane). The polymer was mixed to form a biocompatible solution with an organic polymer hydrogel. The hydrogel was a polyvinylpyrrolidone gel having an average molecular weight of approximately 13,700 and one of a family of such material known as Plasdones. These Plasdones in a molecular weight range of interest are freely transported through tissue fluids and excreted unchanged by the kidneys. The mixture utilized was approximately 38% by weight of the polymer particles and 62% of the gel material. The polymer/gel mixture was mixed until the inert particles were evenly dispersed and then placed in syringes with small pistons placed in the proximal ends. The distal end of each cylinder would have a Luer taper to which an appropriate needle or cannula could be attached. A highly leveraged injection ratchet mechanism was utilized to accept the syringe cartridges and deliver precise amounts of the gel mixture through a cannula into the subcutaneous plane of the ear tissue of 20 large, adult white rabbits. Controls using commercially available collagen derivatives were injected in the subcutaneous plane in adjacent sites in the rabbits' ears using small gauge needles provided by the manufacturers of the collagen derivatives.

With respect to the injected collagen control sites, subsequent histologic sections indicated that after three weeks, no residual collagen could be found at the site of the injection. In dramatic contrast, the histologic sections of the micro particles evidenced a dramatic transition in which the gel phase of the material was replaced by a fibrin and protocollagen matrix surrounding each of the micro particles. In three days, the fibrin matrix was complete, with all the gel having been removed by the host. Connective-tissue cells had developed and had begun to replace the matrix with host collagen fibrils. By the sixth week, this fibrosis was complete, and each individual textured particle appeared to be encased in its own individual inner connected covering of fibrous tissue. The thickness of the implanted area and the degree of fibrosis as measured by transillumination, micrometer and light and electron beam microscopy remained constant for more than a year.

Subsequent histologic examination of the regional lymph nodes at the base of the rabbit ears revealed no migration of particles. Cross-sections of the ear below the injected area showed no particles. Through transillumination, the size and density of the areas of injection were easily and atraumatically monitored for each rabbit. No textured micro implants were found at the base of the ears or in the regional lymph nodes of any of the rabbits under study.

The dimensions of the subcutaneous deposits of textured micro implants remained approximately the same throughout the period of study, as was evidenced by transillumination photographic record and micrometer measurement. Opacity was noted to decrease over the last few weeks as the transillumination became brighter but then appeared to stabilize between the end of the first and the sixth months.

The results obtained with the experimental particles of Example 1 illustrate the dramatic contrast between this material and the injection of collagen-containing materials. Although the collagen-containing materials created immediate soft tissue augmentation, these substances—which are only about 3.5 to 6.5% solid collagen material—soon became invaded by host capillaries and were absorbed. No absorption or migration of the 100, 150 or 600 micron silicone rubber particles was observed, even after 382 days.

In other experiments, particles having an average diameter of 80 microns and incorporating tracer material in the form of gamma radiation-emitting material were injected into the ears of other rabbits. These particles showed no migration from the injection site during a subsequent six-month monitoring period.

While prior work by the inventors and others have shown that surface irregularities preferably are in the 20 to 200 micron range in order to achieve adequate contact guidance of the fibroblasts so as to create or develop a scar tissue pattern that is a mirror image of the substrate surface, it is also appreciated that the particle size in relation to the relative size of the surface irregularities is a factor to be considered. In this connection, if the openings, indentations or pores are too shallow in their depth dimension, or in the event their diameter is not sufficiently great, the fibroblasts will tend to bridge across the defect so as to provide a substantially smooth surface.

In the preferred embodiment of the present invention, the particles indicated or selected for a specific procedure to assist in correcting a given defect are previously loaded into a hypodermic syringe with a needle having an adequately sized interior bore so that upon injection of the needle into the area of the depression being corrected, the particles together with the appropriate physiologic vehicle enables the spheroids to be injected directly into the area of the depression. Appropriate vehicles, as previously indicated, include physiologic saline or polysaccharide lubricants, each of these enabling the spheroids to be injected as set forth.

Figure 4:
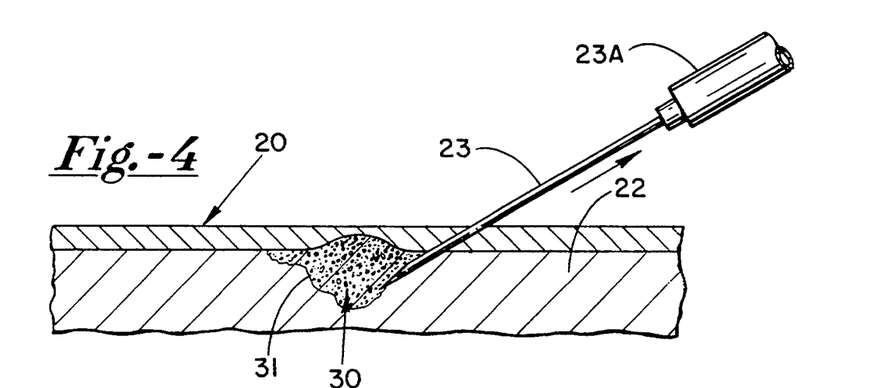
FIG. 4 is a view similar to FIG. 3, and illustrating the same location following subcutaneous injection of the textured micro particles in accordance with the present invention.

With attention being directed to FIG. 3 of the drawings, it will be noted that surface tissue as shown at 20 includes a depression area 21, with the depression area extending into the subcutaneous tissue as at 22. For utilization of the concept of the present invention, the needle 23 is shown as it is injected into tissue. Particles 30, of the type illustrated in FIGS. 1 and 2, along with vehicle 31 are injected into the predetermined site, with the result being filling of the depression area, particularly as illustrated in FIG. 4. Upon withdrawal of the needle 23, the injected material is left in situ at the selected site. The supply of particles 30 is retained in syringe body zone 23A for passage through hollow needle 23.

Figure 7:
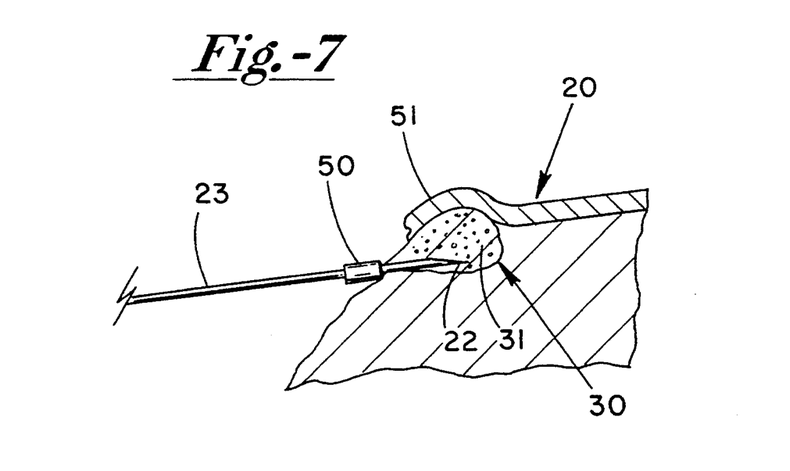
FIG. 7 is a fragmentary schematic view which illustrates the submucosal injection of the microparticles in the vicinity of a bladder neck.

As further illustrated in FIG. 7, the needle 23 may be provided with a marker as at 50, which may be any desired color, to indicate the depth of tissue penetration so that the precise relative location of the needle bevel relative to a bladder neck 51, for example, may be gauged without fluoroscopy.

Syringes of this type are, of course, commercially available, and suitable for particles in the low to mid-size range, while larger particles within the size range may require an inwardly tapered out-flow tract. For certain applications, it has been found desirable to utilize a syringe-needle combination which tapers continuously, thereby providing an elongated syringe-needle combination with a inwardly tapered out-flow tract.

Generally, upon completion of the inflammatory phase of wound healing, or after approximately one week, formation of scar tissue commences with this becoming complete after about three weeks. Following completion of the deposition and formation of scar tissue, a remodeling phase or operation may be undertaken. In view of the specific irregularities and indentations of the surfaces of the individual particles, contact guidance will normally allow for the resulting scar tissue to firmly anchor and attach the implanted particles 30 wherever deposited. As borne out by the example, although various biological substances have been used for similar purposes, such as collagen and fibril, these other previously utilized substances are normally broken down by the body over a period of time and digested autogenously.

It is anticipated that the micro particles fabricated of silicone rubber, polytetrafluoroethylene (Teflon), ceramic or other appropriate inert substances will mimic the durometer hardness of the host tissue being filled, with the softer materials, such as silicone rubber being utilized for normal subcutaneous fat tissue, and with ceramic materials being utilized for bone tissue. Polytetrafluoroethylene (Teflon) is deemed suitable for cartilage, and silicone elastomer with variations in firmness for subcutaneous fat in various regions of the body. In the event the procedure involves an over-correction, the use of lipoplasty techniques of suction lipectomy with a cannula of appropriate diameter will allow for fine tuning, even after several months or years. Removal of an appropriate quantity of filler material may be accomplished in that fashion.

Figure 5:
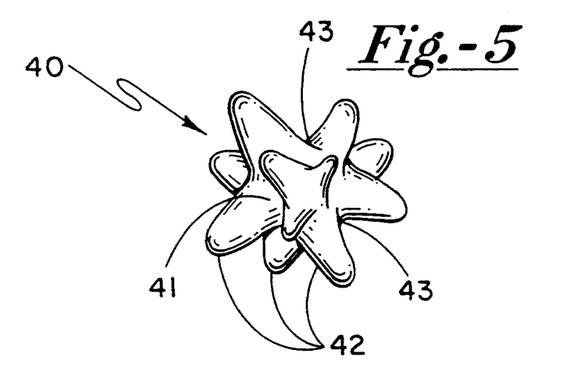
FIG. 5 is a perspective view of a modified form of a useful wherein the surface irregularities project outwardly from a body member in pillar form.
Figure 6:
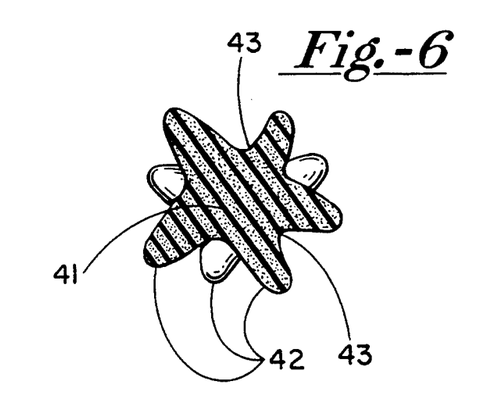
FIG. 6 is a cross-sectional view of the device of FIG. 5.

Specific attention is now directed to the modification of particle configuration illustrated in FIGS. 5 and 6. Specifically, the textured micro particle generally designated 40 comprises a central body portion 41 of generally spheroidal form, together with a number of outwardly projecting pillar members 42—42 thereon. Inter-pillar indentations of generally arcuate form are shown at 43—43. Textured micro particles of the type illustrated in FIGS. 5 and 6 may also be found useful in connection with the various aspects of the present invention. In actual use, these micro particles will be combined with an appropriate vehicle, of the type previously referred to, such as physiologic saline, PVP or polysaccharide lubricant, so as to enable these textured micro particles to be injected into the body. Also, textured micro particles of the type illustrated in FIGS. 5 and 6 may be formed of the same material as indicated in connection with the embodiment of FIGS. 1–4, such as for example, silicone rubber, polytetrafluoroethylene (Teflon), biocompatible solids such as, for example, hydroxyapatite or other biocompatible solids of the type listed hereinabove.

Radiopaque substances such as, for example, barium compounds, may be utilized to make the particles more visible. Radioactive materials may also be incorporated for certain applications. In most instances, however, utilization of such radiographic tagging will not be required.

The foregoing detailed description has been provided directed to the micro particles contemplated in the practice of the present invention to render the instant specification complete in and of itself, without the need for incorporation by reference and/or resort to the cross-referenced application.

As was previously stated, the essence of the present invention is to provide novel procedures for treating urological disorders, particularly stress incontinence and ureteral reflux, wherein textured micro particles of the foregoing description in a biocompatible liquid vehicle are injected endoscopically into submucosal tissue in order to add bulk.

In accordance with the present invention, stress incontinence may be treated by a plurality of spaced injections of the aforementioned micro particles into the submucosal space of the urethra in order to provide the necessary bulk. The amount of the micro particles to be injected will depend at least in part upon the amount of bulk desired for the particular procedure. Accordingly, it is not capable of precise quantification. For this reason, the amount to be injected may be referred to as an "effective amount", meaning an amount effective to provide the desired result. By way of illustration, an "effective amount" in the treatment of stress incontinence is the amount needed to provide the necessary bulk to elevate the mucosa a predetermined desired distance, e.g., on the order of about 2.0 cm.

The procedure, which may be performed under local, regional or general anesthesia, is performed so as to provide a series of mounds which usually include the urethral lumen. The micro particles to be implanted are combined with a biocompatible polymer liquid carrier or vehicle in order to permit the contemplated micro-implant surgery to be accomplished by endoscopic injection.

Thus, according to the present invention, soft tissue augmentation may be obtained by direct cannula injection surgery. Following implantation in the desired submucosa site(s), the micro particle/liquid vehicle combination will undergo a transformation whereby the liquid vehicle component is rapidly scavenged by the host inflammatory cells and then replaced by host fibrin. In this manner, all of the liquid vehicle carrier phase is dispersed by the mammalian host and then completely excreted by the kidneys within a few days. In vivo studies of both animals and humans reported in the literature have shown that massive amounts of the liquid carrier injected intravenously or subcutaneously are promptly excreted from the body chemically unaltered. Examples of these are as follows: Rhodes, J. E.: "Various plasma expanders in man." *Annual, New York Academy of Science,* 55:522–525, 1952; Harwicke, J.: *Advances in Nephrology.* 2:61–74, 1972; Kojima, M., Takahashi, K. & Honda, K.: "Morphological study on the effect of polyvinylpyrrolidone infusion upon the reticuloendothelial system." *Tokyo J. Exp. Med.,* 92:27–54, 1967.

The transformation of the injected substances into specific individual micro-implant particles, each encased in a host collagen lattice occurs in an orderly step-by-step fashion over a relatively short period of time, e.g., over on the order of several weeks. First, as previously stated, the liquid vehicle is replaced by fibrin. Then, the host fibrin is replaced by connective tissue cells which deposit collagen between and through the textured particles.

The following example shows by way of illustration and not by way of limitation procedures steps for treating stress incontinence in accordance with this invention.

EXAMPLE 2

The micro particles/liquid vehicle composition to be injected comprised textured poly(dimethylsiloxane) micro particles ranging generally from about 100–600 micrometers mixed with a PVP gel to provide a biocompatible biphasic solution as described in Example 1. In the following procedure, this solution was contained in a syringe mounted in a pressure injection gun.

1. As desired, local, regional or general anesthesia is administered.
2. The patient is positioned in the lithotomy position.
3. A cystoscope equipped with a panendoscopic lens is inserted into the urethra and the urethra then examined for the suitability of submucosal injection.
4. Assuming suitability, the patient's bladder is then filled with sterile water from on the order of one-fourth to one-half full.
5. A long 16-gauge needle with a cuff one centimeter from the end is passed into the cystoscope or it may be inserted outside the urethra, through the peritoneum, into the region of the bladder neck. The needle is guided by palpitation and visual control through the scope. The syringe mounted in the pressure injection gun and containing the micro particle solution to be injected is attached to the proximal end of the needle.
6. The needle is advanced to the six o'clock position and inserted (bevel up) into the submucosal space, approximately 1–3 cm caudad to the bladder neck, as illustrated in FIG. 7.
7. The position of the needle is checked by inserting a small amount of the micro particle solution. If the needle is properly placed, a bump will appear immediately in the submucosa.
8. If the injection site is correct, approximately 1.0 to 5.0 cc will generally be required per injection site. The injection should elevate the mucosa for a distance of about 2.0 cm. In making the injection, the needle should be held in place for about 30 seconds. The needle is then backed away from the injected material approximately 0.5 cm for 20—20 seconds after the injection is completed in order to seal the injection site.
9. The injection is then repeated at each of the 3 o'clock and 9 o'clock positions and, if necessary, at the 12 o'clock position.

As heretofore mentioned, the final result should be a series of mounds which visually occlude the urethral lumen. This allows the patient to gain needed closure control.

While the invention is particularly directed to the treatment of stress incontinence, it is expressly to be understood that it may also be employed for treatment of other urological disorders by injection of the aforementioned texture micro particle solution. By way of further illustration, it may for example be employed in the correction of vesicoureteral reflux which has heretofore been treated by endoscope injection of polytetrafluoroethylene paste under the intravesical portion of the affected ureter. This is described in, for example, "TECHNICAL REFINEMENTS IN ENDOSCOPIC CORRECTION OF VESICOURETERAL REFLUX", by O'Donnel and Puri, *The Journal of Urology*, vol. 140, November, 1988, pp. 1101–1102.

In accordance with the present invention, endoscopic injection may be made in the same manner as that described in the above-mentioned Urology Journal, substituting applicants' novel textured micro particle solution for the polytetrafluovopthylene parts hereto employed. For example, with the patient positioned with the thighs extended and fully abducted to flatten the case of the bladder, > Insert the needle bevel upwards into about 6 to 10 mm, of the submucosa (lamina propria) at exactly the 6 o'clock position and 5 mm. should be under the ureter itself. After the needle is in place but before injection lift the needle gently under the ureter so that one can outline exactly the position of the point of the needle. It is important not to inject the paste into the muscle of the bladder and not to perforate the ureter. Injection should be done slowly and the effect of each increment should be visualized. The paste is injected until a nipple is created by the paste on top of which sits the now flattened ureteral orifice like an inverted crescent. The volume of paste required varies with the condition of the orifice and the age of the patient. The needle is kept in position for abut 30 seconds after injection to avoid extrusion . . .

As further described in this article, the needle hole may then be irrigated to remove any loose particles of paste.

In general it can be said that the present invention is applicable to the correction of the various urological disorders heretofore treated by endoscopic injection of particles to fill defects and/or provide bulk. Treatment of other urological disorders are also contemplated by the present invention. For example 1 the treatment of post-prostatectomy incontinence and incontinence of females associated with cystourethroceles by intraurethral injection of polytetrafluoroethylene particles is known. (See, for example, "PERIURETHRAL POLYTETRAFLUOROETHYLENE INJECTION FOR URINARY INCONTINENCE", by Politano, *The Journal of Urology*, vol. 127, March, 1982, pp. 439–442.)

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

We claim:

1. A method for long-term treatment of urological and gastric disorders comprising the step of injecting submucosally or peri-urethrally into tissue at at least one injection site a composition comprising an effective amount of relatively soft, malleable, elastic, biologically compatible prosthetic micro particles dispersed in a non-retentive compatible physiological vehicle comprising polyvinyl pyrrolidone, the micro particles of the composition further being of a designed average particle size distribution and characterized by a rough surface having a plurality of surface irregularities generally randomly formed therein, such that the effects of average particle size and average particle surface roughness cooperate in combination in an autogenous manner to essentially prevent loss of the micro particles from any injection site, the particles remaining to be incorporated as long-term tissue augmentation.

2. A method as defined in claim 1 wherein the micro particles possess an average unidimensional particle size in the range of from about 100 microns to about 600 microns.

3. A method as defined in claim 1 wherein the micro particles comprise a polysiloxane.

4. A method as defined in claim 2 wherein the micro particles comprise a polysiloxane.

5. A method as defined in claim 2 wherein the micro particles are polydimethylsiloxane.

6. A method for long-term treatment of incontinence comprising the steps of making a plurality of spaced injections into the submucosal layer of the urethra of a composition comprising an amount of relatively soft, malleable, elastic, biologically compatible prosthetic micro particles dispersed in a non-retentive compatible physiological vehicle comprising polyvinyl pyrrolidone, the micro particles of the composition further being of a designed average unidimensional particle size distribution between 30 and 3000 microns, and characterized by a rough surface having a plurality of surface irregularities generally randomly formed therein, characterized by indentations, cavities and pores forming openings upon the surface of the particles, with the dimensions of the indentations, cavities and pores being generally in a range between 10 angstroms and 500 microns, such that the effects of average particle size and average particle surface roughness cooperate in combination in an autogenous manner to essentially prevent loss of the micro particles from any injection site, the particles remaining to be incorporated as long-term tissue augmentation.

7. A method as defined in claim 6 wherein the micro particles possess an average unidimensional particle size in the range of from about 100 microns to about 600 microns.

8. A method is defined in claim 6 wherein the micro particles comprise a polysiloxane material.

9. A method as defined in claim 7 wherein the micro particles comprise a polysiloxane.

10. A method for long-term treatment of gastric reflux comprising the steps of making a plurality of injections at spaced sites into the appropriate submucosal space selected from the esophageal-gastric junction and gastric-pyloric junction a composition comprising an amount of relatively soft, malleable, elastic, biologically compatible micro particles dispersed in a non-retentive compatible physiological vehicle comprising polyvinyl pyrrolidone, the micro particles of the composition further being of a designed average unidimensional particle size distribution between 30 and 3000 microns, and characterized by a rough surface having a plurality of surface irregularities generally randomly formed therein, characterized by indentations, cavities and pores forming openings upon the surface of the particles, with the dimensions of the indentations, cavities and pores being generally in a range between 10 angstroms and 500 microns, such that the effects of average particle size and average particle surface roughness cooperate in combination in an autogenous manner to essentially prevent loss of the micro particles from any injection site, the particles remaining to be incorporated as long-term tissue augmentation.

11. A method as defined in claim 10 wherein the micro particles possess an average unidimensional particle size in the range of from about 100 microns to about 600 microns.

12. A method is defined in claim 10 wherein the micro particles comprise a polysiloxane material.

13. A method is defined in claim 11 wherein the micro particles comprise a polysiloxane material.

14. A method for long-term treatment of urological and gastric disorders comprising the step of injecting submucosally or peri-urethrally into tissue at at least one injection site a composition comprising an effective amount of relatively soft, malleable, elastic, biologically compatible prosthetic micro particles, characterized by a rough surface having a plurality of irregularities generally randomly formed therein, and dispersed in a non-retentive, non-retained compatible physiological vehicle, wherein the vehicle is eliminated from the injection site and the micro particles being an average particle size distribution and surface roughness such that the effects of average particle size and average particle surface roughness cooperate in combination in an autogenous manner to essentially prevent loss of the micro particles from any injection site, the particles remaining to be incorporated as long-term tissue augmentation.

15. A method as defined in claim 14 wherein the surface irregularities of the micro particles describe indentations, cavities and pores forming a very irregular surface including openings within the particles, the micro particles having an average unidimensional particle size generally between 30 and 3000 microns with the dimensions of the indentations, cavities and pores within the particles being generally in a range between 10 angstroms and 500 microns.

16. The method of claim 15 wherein the vehicle comprises polyvinyl pyrrolidone.

17. A method as defined in claim 15 wherein the micro particles possess an average unidimensional particle size of 100 microns or more.

18. A method as defined in claim 17 wherein the composition is injected into a submucosal space selected from the bladder-urethral junction, the esophageal-gastric junction and the gastric-pyloric junction using a plurality of spaced injection sites.

19. A method as defined in claim 16 wherein the composition is injected under the intravesical portion of the ureter using a plurality of spaced injections.

20. A method as defined in claim 17 wherein the composition is injected under the intravesical portion of the ureter using a plurality of spaced injections.

* * * * *

UNITED STATES PATENT AND TRADEMARK OFFICE
CERTIFICATE OF CORRECTION

PATENT NO. : 5,336,263
DATED : August 9, 1994
INVENTOR(S) : Ersek, et al.

It is certified that error appears in the above-indentified patent and that said Letters Patent is hereby corrected as shown below:

In Column 12, Line 30
  Delete "2.0 cm" and insert -- 2.0 $cm^3$ --;

In Column 12, Line 33
  Delete "include" and insert -- occlude --.

Signed and Sealed this

Eighth Day of October, 1996

Attest:

BRUCE LEHMAN

*Attesting Officer*    *Commissioner of Patents and Trademarks*